US009147250B2

(12) United States Patent
Liu et al.

(10) Patent No.: US 9,147,250 B2
(45) Date of Patent: Sep. 29, 2015

(54) SYSTEM AND METHOD FOR AUTOMATIC MAGNETIC RESONANCE VOLUME COMPOSITION AND NORMALIZATION (75) Inventors: David Liu, Princeton, NJ (US); Shaohua Kevin Zhou, Plainsboro, NJ (US); Peter Gall, Buckenhof (DE); Dorin Comaniciu, Princeton Junction, NJ (US); Andre de Oliveira, Erlangen (DE); Berthold Kiefer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 81 days.

(21) Appl. No.: 13/616,548

(22) Filed: Sep. 14, 2012

(65) Prior Publication Data
US 2013/0072782 A1    Mar. 21, 2013

Related U.S. Application Data (60) Provisional application No. 61/534,996, filed on Sep. 15, 2011.

(51) Int. Cl.
*A61B 5/055* (2006.01)
*G06T 7/00* (2006.01)
*G01R 33/56* (2006.01)
*G01R 33/565* (2006.01)

(52) U.S. Cl.
CPC .......... *G06T 7/0034* (2013.01); *G01R 33/5608* (2013.01); *A61B 5/055* (2013.01); *G01R 33/565* (2013.01); *G06T 2207/10088* (2013.01); *G06T 2207/30004* (2013.01)

(58) Field of Classification Search
CPC ...... A61B 5/055; A61B 6/5241; G01R 33/20; G01R 33/56; G01R 33/5608; G06T 7/00; G06T 15/08; G06T 2207/20221
USPC ........................................................ 600/410
See application file for complete search history.

(56) References Cited

U.S. PATENT DOCUMENTS

| 6,208,138 | B1 | 3/2001 | Lai et al. |
| 6,587,598 | B1 * | 7/2003 | Devillers et al. ............... 382/284 |
| 7,382,908 | B2 | 6/2008 | Dewaele et al. |
| 7,432,707 | B1 | 10/2008 | Boitano |
| 7,782,056 | B2 | 8/2010 | Noterdaeme et al. |
| 7,894,668 | B1 | 2/2011 | Boitano |
| 8,121,366 | B2 | 2/2012 | Valadez et al. |
| 8,155,419 | B2 | 4/2012 | Haider et al. |
| 8,160,319 | B2 | 4/2012 | Holland et al. |

(Continued)

OTHER PUBLICATIONS

Liu, D. and Zhou, K. and Bernhardt, D. and Comaniciu, D., "Search Strategies for Multiple Landmark Detection by Submodular Maximization", IEEE Conference on Computer Vision and Pattern Recognition (CVPR), 2010.

(Continued)

*Primary Examiner* — Jonathan Cwern
*Assistant Examiner* — Amelie R Gillman (57) ABSTRACT A method and system for automatic magnetic resonance (MR) volume composition and normalization is disclosed. In one embodiment, a plurality of MR volumes is received. A composite MR volume is generated from the plurality of MR volumes. Volume normalization of the composite MR volume is then performed to correct intensity inhomogeneity in the composite MR volume. The volume normalization of the composite MR volume may be performed using template MR volume or without a template MR volume.

39 Claims, 7 Drawing Sheets

Before Normalization    After Normalization

(56) References Cited

U.S. PATENT DOCUMENTS

| | | |
|---|---|---|
| 8,175,349 B2 | 5/2012 | Jerebko |
| 8,184,879 B2 | 5/2012 | Geier et al. |
| 8,213,715 B1 | 7/2012 | Boitano |
| 8,217,652 B2 | 7/2012 | Dannels |
| 8,224,048 B2 | 7/2012 | Hou et al. |
| 8,224,420 B2 | 7/2012 | Mu et al. |
| 8,634,623 B2* | 1/2014 | Schmitt et al. ............ 382/131 |
| 2007/0012880 A1* | 1/2007 | Haider et al. ............ 250/363.02 |
| 2008/0108893 A1* | 5/2008 | Krishnan et al. ............ 600/415 |
| 2009/0030302 A1* | 1/2009 | Taniguchi et al. ............ 600/410 |
| 2009/0046915 A1* | 2/2009 | Hou et al. ............ 382/131 |
| 2010/0054572 A1* | 3/2010 | Tsougarakis et al. ............ 382/131 |
| 2010/0061612 A1* | 3/2010 | Reisman et al. ............ 382/131 |
| 2010/0128952 A1* | 5/2010 | Schmitt et al. ............ 382/131 |
| 2011/0116694 A1* | 5/2011 | Gareau ............ 382/128 |
| 2013/0336553 A1* | 12/2013 | Buisseret et al. ............ 382/128 |

OTHER PUBLICATIONS

Vovk, U. and Pernus, F. and Likar, B., "A review of methods for correction of intensity inhomogeneity in MRI", IEEE Trans. on Medical Imaging, vol. 26 (3), 2007.

* cited by examiner

Before Normalization    After Normalization

SYSTEM AND METHOD FOR AUTOMATIC MAGNETIC RESONANCE VOLUME COMPOSITION AND NORMALIZATION

This application claims the benefit of U.S. Provisional Application No. 61/534,996, filed Sep. 15, 2011, the disclosure of which is herein incorporated by reference.

BACKGROUND OF THE INVENTION

The present invention relates to composition and normalization of magnetic resonance (MR) volume data, and more particularly, to automatic composition and normalization of MR volume data.

Magnetic Resonance (MR) is a well known technique for imaging internal structures of a human body. MR scanners are used to scan portions of the human body, resulting in MR volume representing the scanned portions of the body. In some cases, a set of MR volumes covering the whole or part of a body of the patient are obtained using multiple scans. It is then necessary to generate a composite MR image of the patient's body, referred to as a composite MR volume.

Whole-body images in magnetic resonance imaging (MRI) can be generated by combining multiple volumes, also called volume composition. The individual volumes that are being combined have a certain overlap with each other. The overlapping voxels provide the basic information for the composition.

Combining multiple volumes results in generation of the composite MR volume that may include a plurality of the intensity inhomogeneity (IIH) or intensity non-uniformity regions. IIH refers to the slow intensity variation of the same tissue over the volume. This artifact can be due to patient movements, radio-frequency non-uniformity, static-field inhomogeneity, etc. IIH is present in the individual volumes before volume composition is performed. Automated image analysis methods such as those in CAD systems can benefit from an IIH correction step, since IIH could have negative impact on the image analysis algorithm. The presence of IIH can reduce the accuracy of image segmentation and registration, hence decreasing the reliability of subsequent quantitative measurement. IIH has previously been considered in the context of a single volume (before volume composition).

BRIEF SUMMARY OF THE INVENTION

The present invention provides a method and system for automatic composition and normalization of MR volume data. Embodiments of the present application disclose performing IIH correction or normalization after composition of the composite MR volume. An advantage of such embodiments is that the field of view becomes much larger after volume composition, which means more voxels can be observed and hence more information can be obtained for IIH correction.

In one embodiment, a plurality of MR volumes is received. A composite MR volume is generated from the plurality of MR volumes. Volume normalization of the composite MR volume is then performed to correct intensity inhomogeneity in the composite MR volume. The volume normalization of the composite MR volume may be performed using template MR volume or without a template MR volume.

According to another embodiment of the present invention, the volume normalization of the composite MR volume is performed without using templates. The volume normalization of the composite MR volume without using templates is a two-step process in which the first step is a normalization of the composite MR volume being performed along one particular axis and where the second step is a normalization of the composite MR volume being performed along one other particular axis.

The advantages of the present invention will be apparent to those of ordinary skill in the art by reference to the following detailed description and the accompanying drawings.

DETAILED DESCRIPTION

The present invention is directed to a method for automatic composition and normalization of magnetic resonance (MR) volumes. Embodiments of the present invention are described herein to give a visual understanding of the composition and normalization method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. For example, according to various embodiments of the present invention, electronic data representing MR volumes is manipulated within a computer system.

According to embodiments of the present invention, the multiple MR volumes are automatically merged in order to generate a composite MR image of the patient's body. The MR volumes may be stored in the DICOM format, which is a well known medical image file format.

Figure 1:
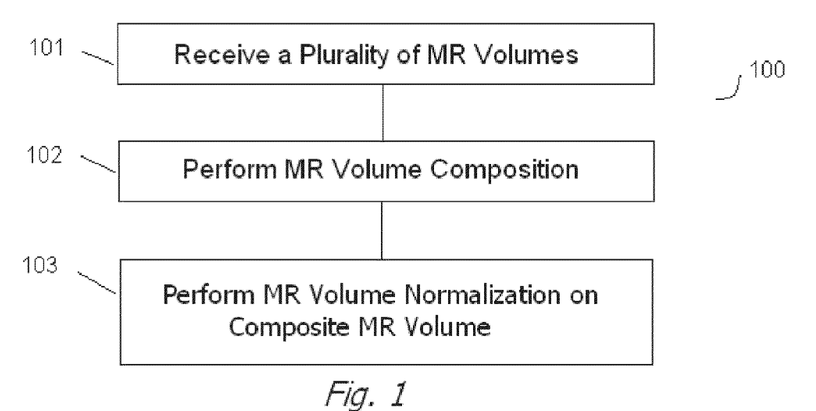
FIG. 1 illustrates a method for automatic composition and intensity normalization of magnetic resonance (MR) volumes.
Figure 2:
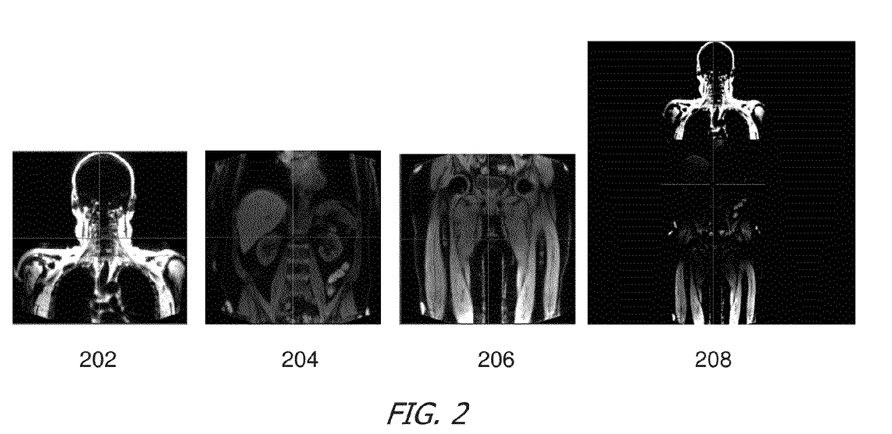
FIG. 2 illustrates an exemplary set of MR volumes that are subject to volume composition and intensity normalization and composite MR volume which is subject to intensity normalization.

FIG. 1 illustrates a method 100 for automatic composition and normalization of magnetic resonance (MR) volumes according to an embodiment of the present invention. At step 101, a plurality of MR volumes is selected. The plurality of MR volumes is obtained in a plurality of MR scans, each corresponding to a different region of the same patient. The MR volume can be received directly from an MR scanning device or by loading previously stored MR volumes. The MR volumes may be in the DICOM format, which is a well known medical image file format. FIG. 2 illustrates an exemplary set of MR volumes that are subject to composition and normalization using the method of FIG. 1. As shown in FIG. 2, images 202, 204, and 206 are slices of MR volumes resulting from MR scans of three different regions of the same patient.

Returning to FIG. 1, at step 102, MR volume composition is performed to interconnect the plurality of MR volumes into a single composite MR volume. According to an advantageous embodiment of the present invention, the MR volume composition is performed prior to normalization of the individual MR volumes.

Figure 3:
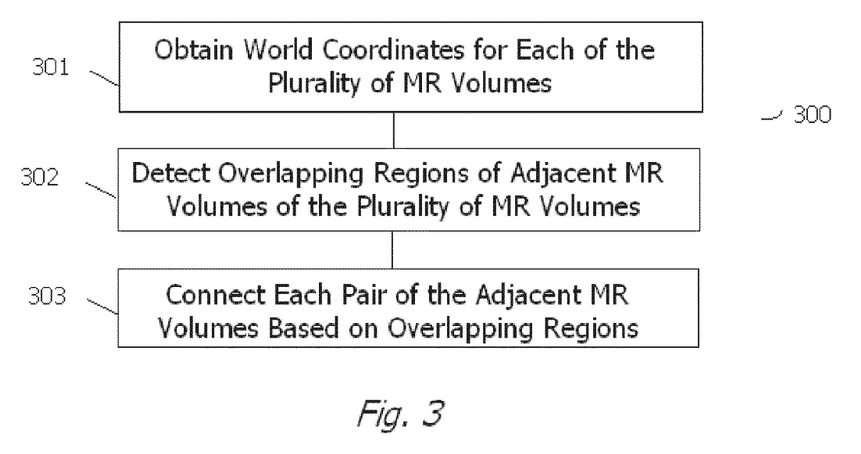
FIG. 3 illustrates a method for automatic composition of MR volumes according to an embodiment of the present invention.

FIG. 3 illustrates method 300 for automatic composition of MR volumes according to an embodiment of the present invention. The method of FIG. 3 can be used to implement step 102 of FIG. 1 in order to interconnect the plurality of MR volumes. It is to be understood that method 300 can be repeated multiple times in order to align a large number of MR volumes. At step 301, a world coordinate is obtained for each of the plurality of MR volumes through the DICOM tags. Once the world coordinate is obtained for each MR volume, the relative position between all of the MR volumes is known. However, the DICOM world coordinates tags alone are not sufficient for accurate volume composition.

At step 302, overlapping parts between adjacent MR volumes are detected. This is achieved by maximizing the normalized cross correlation between the overlapping parts of adjacent MR volumes. Denote the first MR volume by $V_1$, and the second MR volume by $V_2$. The overlapping parts are denoted by $C_1$ and $C_2$, respectively. In practice, $C_1$ and $C_2$ have different appearance, due to (1) non-rigid deformation of patient's body when $V_1$ and $V_2$ are acquired, and (2) imaging artifacts are inhomogeneous at different parts of the scanner. Since the appearance of $C_1$ and $C_2$ would not match exactly, to find the best match an optimization function is invoked. In an embodiment of the present application, a search for $C_1$ within $V_1$ and $C_2$ within $V_2$ is performed in order to satisfy the following criteria: $(C^*_1, C^*_2) = \arg\max NCC(C_1, C_2)$ where NCC is the normalized cross-correlation function:

$$NCC(C_1, C_2) = \left\langle \frac{C_1}{\|C_1\|}, \frac{C_2}{\|C_2\|} \right\rangle,$$

where $\|\cdot\|$ is the $L^2$ norm and $\langle .,. \rangle$ is the inner product.

At step 303, each pair of adjacent MR volumes is connected based on the detected overlapping parts. With $C_1$ and $C_2$ detected at step 302, the connection of each pair of adjacent MR volumes is achieved by $V_1$ being translated relative to $V_2$ so that $C_1$ and $C_2$ overlap precisely. To ensure a smooth transition, voxel intensities are blended through a linear combination, $I(z)=\alpha(z)C_1(z) (1\alpha(z+))C_2-(z)$ where $z \in [0, Dim_z(C_i)]$ is the z-coordinate of cropped volume $C_i$, $\alpha(z) \in [0,1]$ is a linear function of z, and I(z) is the blended voxel intensity for voxels with z-coordinate equal to z.

The method of FIG. 3 results in a single composite MR volume generated by connecting the plurality of MR volumes. Image 208 of FIG. 2 is a slice of the composite MR volume generated from the three MR volumes shown images 202, 204, and 206 using the method of FIG. 3. As shown in the images 202, 204, and 206 of FIG. 2, the intensities windows were set separately and differently from each volume in order to clearly visualize each volume. As shown in image 208, where the three volumes are combined without IIH normalization, intensities inhomogeneity can be observed along the vertical axis, as well as in the transverse planes of the composite MR volume.

Returning to FIG. 1, at step 103, the composite MR volume is normalized to correct intensity inhomogeneity (IIH) in the composite MR volume.

In one embodiment of the present invention, automatic normalization is performed using one or more stored template MR volumes, where a template MR volume is a volume which has been previously normalized. A template MR volume can be created from a previously generated composite MR volume. Specifically, using a viewer that is capable of displaying coronal cross sections of composite MR volume, discontinuities of intensities along the Z-axis can be observed. To remove such a discontinuity, a set of points {p} can be specified by a user in any cross section that should have identical intensity values $I_{desired}$. Such an assumption of identical intensity values follows from the physical principle that identical tissues should have the same physical tissue parameters, and hence their MR intensity values should be similar. Assume the points are placed densely at coordinates $(x_1, y_1, z_1), \ldots, (x_N, y_N, z_N)$, with corresponding intensity values $I_1, \ldots, I_N$. Since dense placement of such points is time-consuming, standard interpolation schemes, such as linear interpolation, or piecewise cubic spline interpolation can be used to obtain an estimated intensity value $I_i$ for arbitrary z values. For example, using such interpolation techniques, at least one point is placed on each horizontal slice of the volume.

Once an intensity value is obtained for each slice, the intensity of the pixels belonging to that slice can be modified so that at slice $z=z_i$, pixels with original intensity value $I_i$ become $I_{desired}$. This can be achieved by scaling the intensities linearly: $I \leftarrow I \times I_{desired}/I_i$. As may be appreciated, more complex schemes can be derived when linear scaling does not yield a satisfactory result. For example, if the user places K sets of points corresponding to K different tissue types, each tissue type with desired intensity values $I_{d_1}, \ldots, I_{d_k}$, then the intensity adjustment formula can be modified into piecewise linear scaling. It should be noted that the template volume needs only be created once. Subsequently, given any novel volume, such as the composite volume generated at step 102 of FIG. 1, fully automatic intensity normalization can obtained using the stored template volume.

Figure 4:
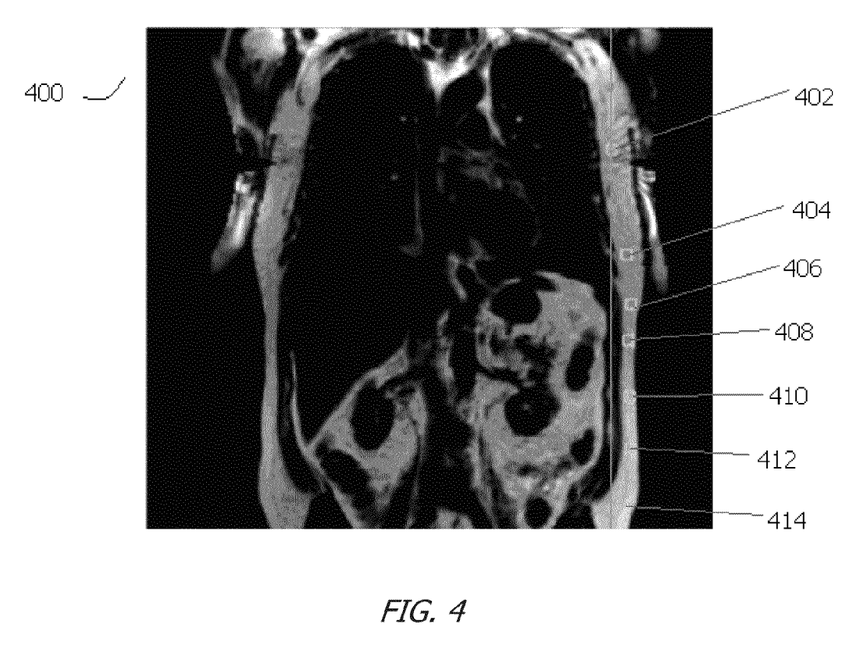
FIG. 4 illustrates an exemplary template creation procedure.

FIG. 4 illustrates an exemplary template creation procedure. A set of points 402, 404, 406, 408, 410, 412, and 414 is placed densely at specific coordinates in a cross section 400 which should have identical intensity values. Placement of points may be performed in manual or automatic modes. As described above, once an intensity value is obtained for each slice, the intensity of the pixels belonging to that slice can be modified so that pixels with original intensity value become pixels with desired intensity value. This can be achieved by scaling the intensities linearly.

Figure 5:
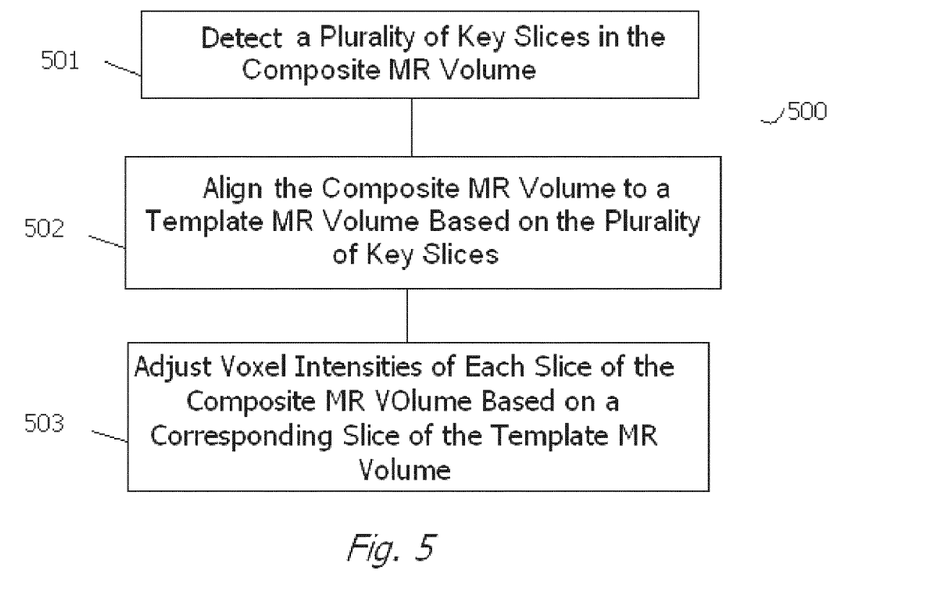
FIG. 5 illustrates a method of automatic intensity normalization of MR volumes using templates according to an embodiment of the present invention.

FIG. 5 illustrates a method 500 of automatic normalization of a composite MR volume using a template MR volume according to an embodiment of the present invention. The method of FIG. 5 can be used to implement step 103 of FIG. 1.

At step 501, a plurality of key slices is detected in the composite MR volume. Examples of key slices include the slice that passes through the top of the liver and the slice that pass through the top of the lung. The detection of key slices can be fully automated by using a learning based landmark detection system, such as the landmark detection system described in U.S. Patent Publication Application No. 2010/0080434 which is incorporated herein by reference.

At step 502, the composite MR volume is aligned to the template MR volume based on the plurality of key slices. The two volumes are aligned so the key slices detected in the composite MR volume are mapped to corresponding slices in the template volume. It should be noted that corresponding slices means slices that are related to the same organ positions. After the key slices are aligned to the template volume, the remaining slices in the composite MR volume are mapped to the template volume by linearly interpolating their position with respect to the key slices. As a result, each slice in the novel volume is mapped to a corresponding slice in the template volume.

Figure 6:
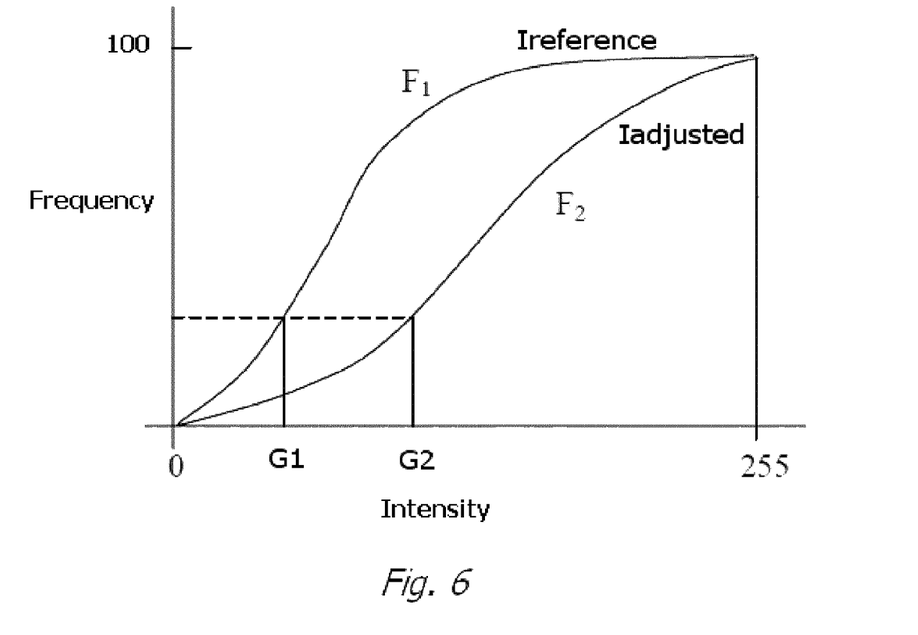
FIG. 6 illustrates an exemplary method for a histogram adjustment of the voxel intensities.

At step 503, voxel intensities within each slice of the composite MR volume are adjusted based on the corresponding slices of the template MR volume. The adjustment of the voxel intensities within each slice of the composite MR volume is achieved through histogram adjustment as illustrated in FIG. 6. As shown in FIG. 6, the adjusted histogram F2 is the intensity histogram obtained from a slice of the composite MR volume. The reference histogram F1 is the intensity histogram obtained from its corresponding slice of the template volume. The histogram adjustment maps the voxel intensities of voxels in the slice of the composite MR volume from value G2 to a value G1 of voxel intensities occurring at the same frequency in the corresponding slice of the template volume so that the two histograms match each other. Histogram adjustment is used to adjust each slice of the composite MR volume, which results in a normalizing composite MR volume.

Figure 7:
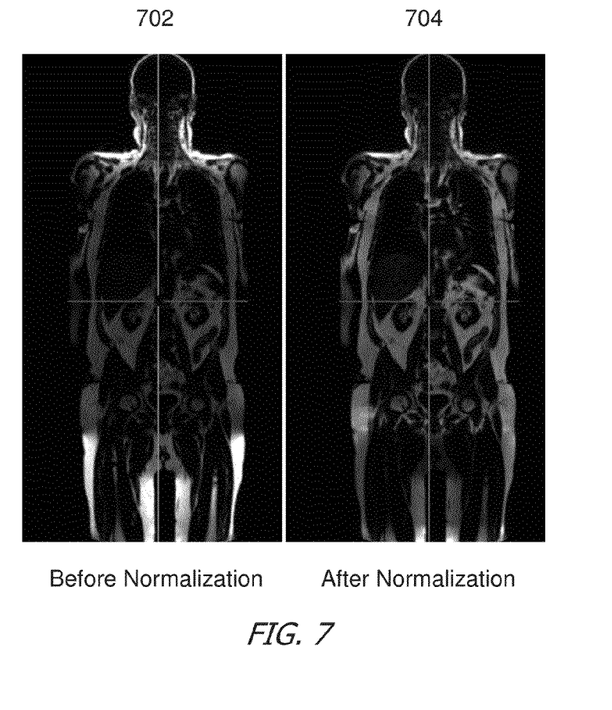
FIG. 7 illustrates exemplary images of composite MR volume before intensity normalization and after intensity normalization using templates.

FIG. 7 illustrates exemplary results of normalization of composite MR volume using a template MR volume. As illustrated in FIG. 7, an image 702 illustrates a composite MR volume prior to normalization. Image 702 features visibly intensity inhomogeneity throughout the composite MR volume. Image 704 illustrates the composite MR volume after normalization using a template MR volume is completed.

In an alternative embodiment of the present invention, the composite MR volume is normalized without a template. Normalization without a template may be advantageous when the target patient exhibits strong pathologies and has very distinct visual appearance from the template volume or when templates are not readily available.

Figure 8:
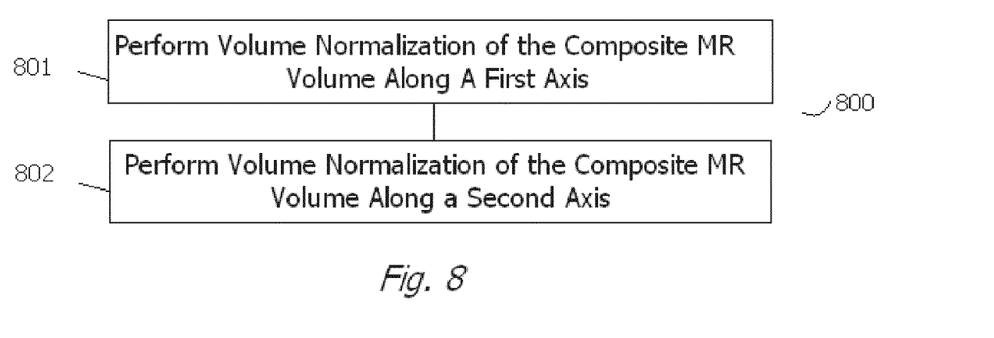
FIG. 8 illustrates a method for a method of automatic intensity normalization of MR volumes without using templates according to an embodiment of the present invention.

FIG. 8 illustrates a method 800 for automatic normalization of MR volumes without using templates according to an embodiment of the present invention. The method 800 of FIG. 8 can be used to implement step 103 of FIG. 1. At step 801, normalization along a first axis is performed. For example, normalization is performed along y-axis (i.e., anterior-posterior), using coronal planes. In order to perform normalization along the y-axis, the muscle intensity in each coronal slice of the composite MR volume is approximated by the median intensity of voxels from that coronal slice of the composite MR volume. Voxel intensities in each coronal slice are then adjusted by stretching (linearly scaling) the voxel intensity histogram of each coronal slice so that the approximated muscle intensity is constant along the y-axis. That is, the voxel intensities in each coronal slice are adjusted so that the median intensity in each coronal slice is equal. For example, if the median intensity in a first slice has a value X, and the median intensity in the second slice has a value Y, then each voxel in the second slice can be scaled by the ratio (Y/X). This ensures that the median intensity of the second slice is equal to the first slice. The same operation is extended to all slices.

Figure 9:
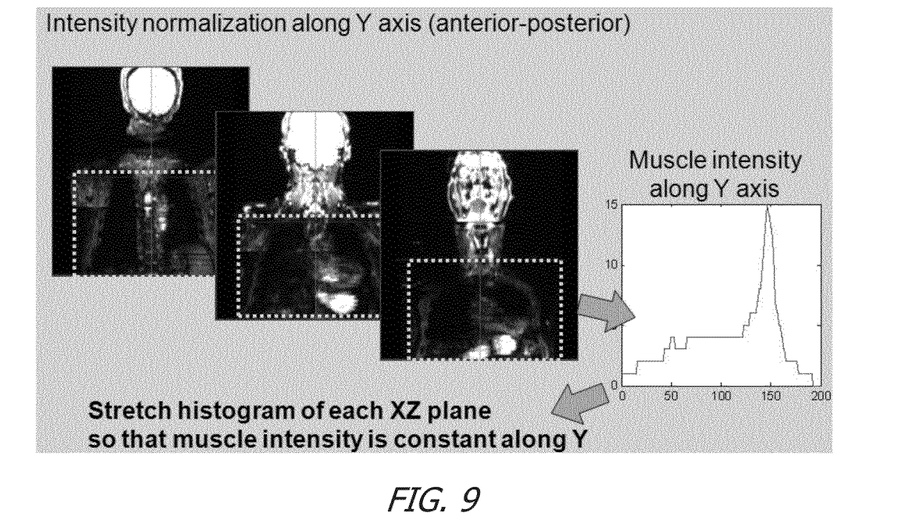
FIG. 9 illustrates an exemplary process of intensity normalization of MR volumes along Y axis.

FIG. 9 illustrates an exemplary process of intensity normalization of MR volumes along the y-axis (anterior-posterior) without using templates.

Figure 10:
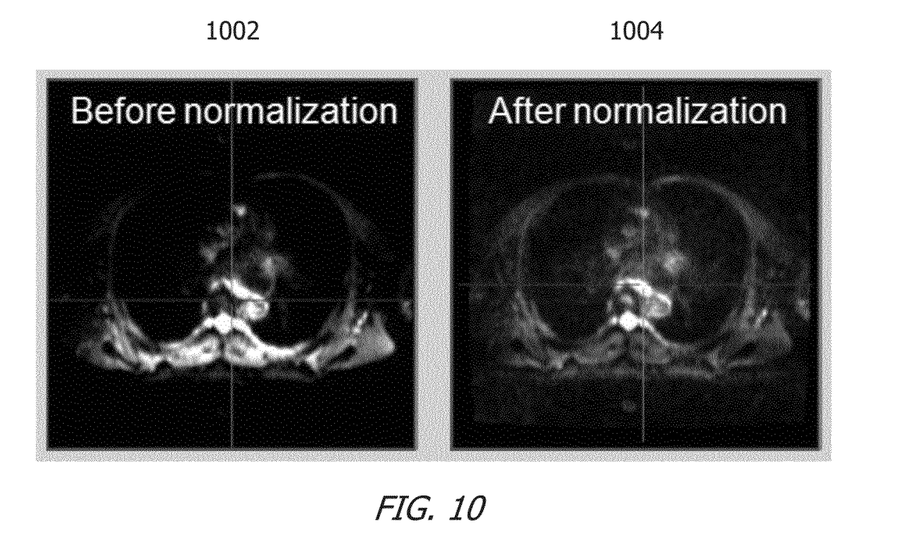
FIG. 10 illustrates an exemplary images of composite MR volume before intensity normalization and after intensity normalization along Y axis.

FIG. 10 illustrates exemplary images of a composite MR volume before intensity normalization and after intensity normalization along y-axis as implemented at steps 801 of the method 800 in FIG. 8 and as shown in FIG. 9. Image 1002 of FIG. 10 illustrates a composite MR volume prior to normalization. Image 1004 of FIG. 10 illustrates the composite MR volume after normalization along anterior-posterior axis without using templates is completed.

Figure 11:
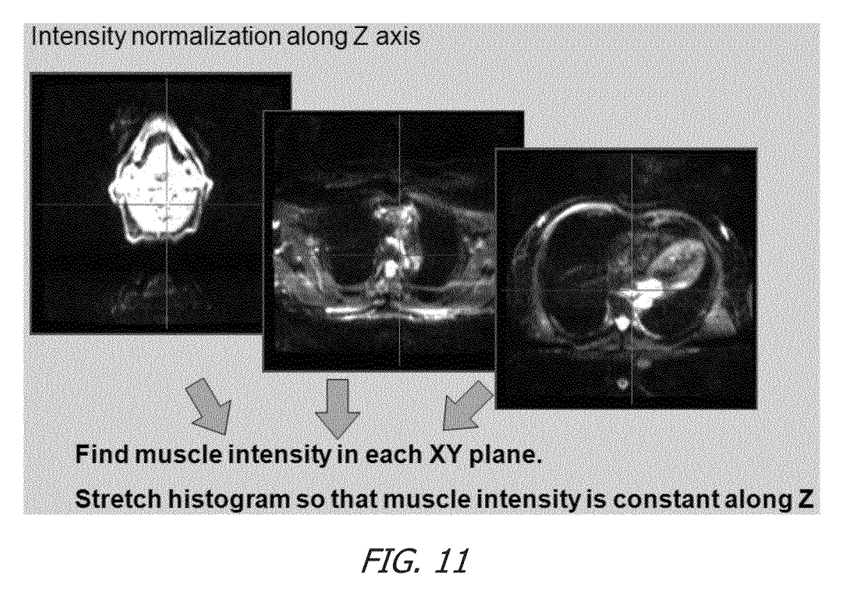
FIG. 11 illustrates an exemplary process of intensity normalization of MR volumes along Z axis.

Returning to FIG. 8, at step 802, normalization along a second axis is performed. For example, normalization is performed along the z-axis (vertical axis), using transverse planes. In order to perform normalization along the z-axis, the muscle intensity in each transverse slice is approximated by the median intensity of voxels from that transverse slice of the composite MR volume. Voxel intensities in each transverse slice are then adjusted by linearly scaling the voxel intensity histogram of each transverse slice so that the approximated muscle intensity is constant along the z-axis. That is, the voxel intensities in each transverse slice are adjusted so that the median intensity in each transverse slice is equal. FIG. 11 illustrates exemplary method of normalization along z-axis described in step 802 of the method 800 in FIG. 8.

Figure 12:
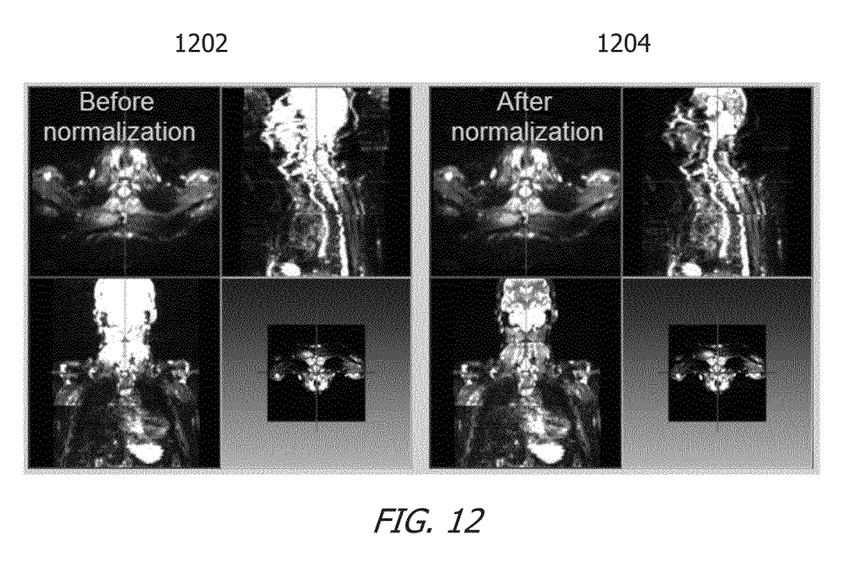
FIG. 12 illustrates exemplary images of composite MR volume after intensity normalization along Z axis.

FIG. 12 illustrates exemplary images of composite MR volume after intensity normalization along the Z axis using transverse planes. Images 1202 of FIG. 12 illustrate slices of a composite MR volume prior to normalization along the Z axis. Images 1204 of FIG. 12 illustrate the slices of the composite MR volumes after normalization along the Z axis is completed.

Figure 13:
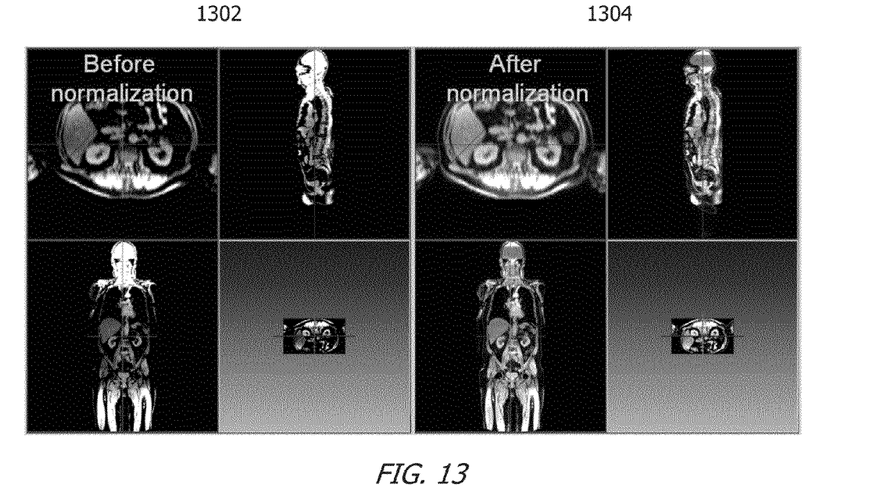
FIG. 13 illustrates an exemplary images of composite MR volume after intensity normalization process.

It should be noted that steps 801 and 802 of FIG. 8 can be performed iteratively several times, however satisfactory results can be obtained after the first iteration of the volume normalization process 800. FIG. 13 illustrates exemplary images of composite MR volume after intensity normalization along Y axis and along Z axis using the method 800 of FIG. 8. Images 1302 of FIG. 13 illustrate slices of a composite MR volume prior to normalization along Y axis and along Z axis. Images 1304 of FIG. 13 illustrate the slices of the composite MR volume after normalization along Y axis and along Z axis is completed.

Figure 14:
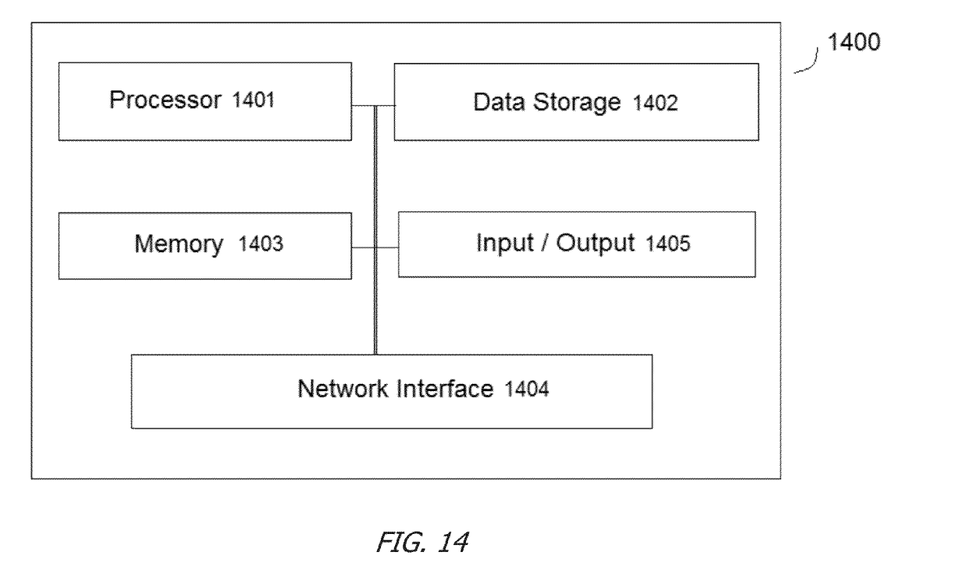
FIG. 14 is an exemplary high level block diagram of a computer capable of implementing the present invention.

The above-described methods for composing and normalizing MR volumes can be implemented on a computer using well-known computer processors, memory units, storage devices, computer software, and other components. A high level block diagram of such a computer is illustrated in FIG. 14. Computer 1400 contains a processor 1401 which controls the overall operation of the computer 1400 by executing computer program instructions which define such operation. The computer program instructions may be stored in a storage device 1402 (e.g., magnetic disk) and loaded into memory 1403 when execution of the computer program instructions is desired. Thus, applications for performing the above described method steps can be defined by the computer program instructions stored in the memory 1403 and/or storage 1402 and controlled by the processor 904 executing the computer program instructions. Furthermore, image data corresponding to MR volumes can be stored in the memory 1403 and/or the storage 1402. An MR scanning device which generates MR images can be connected to the computer 1400 to input MR images to the computer 1400. It is possible to implement the MR scanning device and the computer 1400 as one device. It is also possible the MR scanning device and the computer 1400 communicate wirelessly through a network. The computer 1400 also includes one or more network interfaces 1404 for communicating with other devices via a network. The computer 1400 also includes other input/output devices 1405 that enable user interaction with the computer 1400 (e.g., display, keyboard, mouse, speakers, buttons, etc.)

One skilled in the art will recognize that an implementation of an actual computer or computer system may have other structures and may contain other components as well, and that FIG. 14 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for automatic magnetic resonance (MR) volume composition and normalization comprising:
    receiving a plurality of MR volumes;
    generating a composite MR volume from the plurality of MR volumes; and
    performing volume normalization of the composite MR volume to correct intensity inhomogeneity in the composite MR volume, wherein performing volume normalization of the composite MR volume comprises:
        detecting key slices from a plurality of slices in the composite MR volume;
        aligning each of the plurality of slices in the composite MR volume to a corresponding slice of a template MR volume based on the key slices; and
        adjusting voxel intensities in each of the plurality of slices of the composite MR volume based on the corresponding slice of the template MR volume.

2. The method of claim 1, wherein generating the composite MR volume comprises:
    generating the composite MR volume from the plurality of MR volumes without normalizing the plurality of MR volumes prior to generating the composite MR volume.

3. The method of claim 2, wherein generating the composite MR volume comprises:
    obtaining world coordinates for each of the plurality MR volumes;
    locating overlapping regions of adjacent MR volumes of the plurality of MR volumes based on the world coordinates; and
    connecting the overlapping regions of the adjacent MR volumes.

4. The method of claim 3, wherein connecting the overlapping regions in the adjacent MR volumes comprises:
    detecting corresponding voxels in the overlapping regions of the adjacent MR volumes; and
    blending intensities of the corresponding voxels in the overlapping regions of the adjacent MR volumes.

5. The method of claim 4, wherein detecting corresponding voxels in the overlapping regions of the adjacent MR volume comprises:
    maximizing a normalized cross-correlation between the overlapping regions of the adjacent MR volumes.

6. The method of claim 1, wherein adjusting voxel intensities in each of the plurality of slices of the composite MR volume comprises:
    adjusting voxel intensities of voxels in each of the plurality of slices of the composite MR volume such that an intensity histogram of each of the plurality of slices of the composite MR volume matches an intensity histogram of the corresponding slice of the template MR volume.

7. A method for automatic magnetic resonance (MR) volume composition and normalization comprising:
    receiving a plurality of MR volumes;
    generating a composite MR volume from the plurality of MR volumes; and
    performing volume normalization of the composite MR volume to correct intensity inhomogeneity in the composite MR volume, wherein performing volume normalization of the composite MR volume comprises:
        normalizing slices of the composite MR volume along a first axis based on approximated muscle intensity in each of the slices along the first axis, and
        normalizing slices of the composite MR volume along a second axis based on approximated muscle intensity in each of the slices along the second axis.

8. The method of claim 7, wherein normalizing slices of the composite MR volume along the first axis comprises:
    approximating the muscle intensity in each slice of the composite MR volume along the first axis as the median intensity of voxels in that slice; and
    adjusting voxel intensities in each slice of the composite MR volume along the first axis so that the approximated muscle intensity is constant along the first axis.

9. The method of claim 8, wherein adjusting voxel intensities in each slice of the composite MR volume along the first axis comprises:
    linearly scaling a voxel intensity histogram of each slice of the composite MR volume along the first axis.

10. The method of claim 8, wherein normalizing slices of the composite MR volume along the second axis comprises:
    approximating the muscle intensity in each slice of the composite MR volume along the second axis as the median intensity of voxels in that slice; and
    adjusting voxel intensities in each slice of the composite MR volume along the second axis so that the approximated muscle intensity is constant along the second axis.

11. The method of claim 10, wherein adjusting voxel intensities in each slice of the composite MR volume along the second axis comprises:
    linearly scaling a voxel intensity histogram of each slice of the composite MR volume along the second axis.

12. The method of claim 10, wherein the slices of the composite MR volume along the first axis are coronal slices and the slices of the composite MR volume along the second axis are transverse slices.

13. The method of claim 7, wherein the first axis is an anterior-posterior axis and the second axis is a vertical axis.

14. An apparatus for automatic magnetic resonance (MR) volume composition and normalization comprising:
    a memory storing computer program instructions; and
    a processor communicatively coupled to the memory, the processor configured to execute the computer program instructions, which, when executed on the processor, cause the processor to perform operations comprising:
        receiving a plurality of MR volumes;

generating a composite MR volume from the plurality of MR volumes; and performing volume normalization of the composite MR volume to correct intensity inhomogeneity in the composite MR volume, wherein performing volume normalization of the composite MR volume comprises:

detecting key slices from a plurality of slices in the composite MR volume;

aligning each of the plurality of slices in the composite MR volume to a corresponding slice of a template MR volume based on the key slices; and adjusting voxel intensities in each of the plurality of slices of the composite MR volume based on the corresponding slice of the template MR volume.

15. The apparatus of claim 14, wherein generating the composite MR volume comprises:

generating the composite MR volume from the plurality of MR volumes without normalizing the plurality of MR volumes prior to generating the composite MR volume.

16. The apparatus of claim 15, wherein generating the composite MR volume comprises:

obtaining world coordinates for each of the plurality MR volumes;

locating overlapping regions of adjacent MR volumes of the plurality of MR volumes based on the world coordinates; and connecting the overlapping regions of the adjacent MR volumes.

17. The apparatus of claim 16, wherein connecting the overlapping regions in the adjacent MR volumes comprises:

detecting corresponding voxels in the overlapping regions of the adjacent MR volumes; and blending intensities of the corresponding voxels in the overlapping regions of the adjacent MR volumes.

18. The apparatus of claim 17, wherein detecting corresponding voxels in the overlapping regions of the adjacent MR volume comprises:

maximizing a normalized cross-correlation between the overlapping regions of the adjacent MR volumes.

19. The apparatus of claim 14, wherein adjusting voxel intensities in each of the plurality of slices of the composite MR volume comprises:

adjusting voxel intensities of voxels in each of the plurality of slices of the composite MR volume such that an intensity histogram of each of the plurality of slices of the composite MR volume matches an intensity histogram of the corresponding slice of the template MR volume.

20. An apparatus for automatic magnetic resonance (MR) volume composition and normalization comprising:

a memory storing computer program instructions; and a processor communicatively coupled to the memory, the processor configured to execute the computer program instructions, which, when executed on the processor, cause the processor to perform operations comprising:

receiving a plurality of MR volumes;

generating a composite MR volume from the plurality of MR volumes; and performing volume normalization of the composite MR volume to correct intensity inhomogeneity in the composite MR volume, wherein performing volume normalization of the composite MR volume comprises:

normalizing slices of the composite MR volume along a first axis based on approximated muscle intensity in each of the slices along the first axis, and normalizing slices of the composite MR volume along a second axis based on approximated muscle intensity in each of the slices along the second axis.

21. The apparatus of claim 20, wherein normalizing slices of the composite MR volume along the first axis comprises:

approximating the muscle intensity in each slice of the composite MR volume along the first axis as the median intensity of voxels in that slice; and adjusting voxel intensities in each slice of the composite MR volume along the first axis so that the approximated muscle intensity is constant along the first axis.

22. The apparatus of claim 21, wherein adjusting voxel intensities in each slice of the composite MR volume along the first axis comprises:

linearly scaling a voxel intensity histogram of each slice of the composite MR volume along the first axis.

23. The apparatus of claim 21, wherein normalizing slices of the composite MR volume along the second axis comprises:

approximating the muscle intensity in each slice of the composite MR volume along the second axis as the median intensity of voxels in that slice; and adjusting voxel intensities in each slice of the composite MR volume along the second axis so that the approximated muscle intensity is constant along the second axis.

24. The apparatus of claim 23, wherein adjusting voxel intensities in each slice of the composite MR volume along the second axis comprises:

linearly scaling a voxel intensity histogram of each slice of the composite MR volume along the second axis.

25. The apparatus of claim 23, wherein the slices of the composite MR volume along the first axis are coronal slices and the slices of the composite MR volume along the second axis are transverse slices.

26. The apparatus of claim 20, wherein the first axis is an anterior-posterior axis and the second axis is a vertical axis.

27. A non-transitory computer readable medium storing computer program instructions, which, when executed on a processor, cause the processor to perform operations comprising:

receiving a plurality of magnetic resonance (MR) volumes;

generating a composite MR volume from the plurality of MR volumes; and performing volume normalization of the composite MR volume to correct intensity inhomogeneity in the composite MR volume, wherein performing volume normalization of the composite MR volume comprises:

detecting key slices from a plurality of slices in the composite MR volume;

aligning each of the plurality of slices in the composite MR volume to a corresponding slice of a template MR volume based on the key slices; and adjusting voxel intensities in each of the plurality of slices of the composite MR volume based on the corresponding slice of the template MR volume.

28. The non-transitory computer readable medium of claim 27, wherein generating the composite MR volume comprises:

generating the composite MR volume from the plurality of MR volumes without normalizing the plurality of MR volumes prior to generating the composite MR volume.

29. The non-transitory computer readable medium of claim 28, wherein generating the composite MR volume comprises:

obtaining world coordinates for each of the plurality MR volumes;

locating overlapping regions of adjacent MR volumes of the plurality of MR volumes based on the world coordinates; and connecting the overlapping regions of the adjacent MR volumes.

30. The non-transitory computer readable medium of claim 29, wherein connecting the overlapping regions in the adjacent MR volumes comprises:

detecting corresponding voxels in the overlapping regions of the adjacent MR volumes; and blending intensities of the corresponding voxels in the overlapping regions of the adjacent MR volumes.

31. The non-transitory computer readable medium of claim 30, wherein detecting corresponding voxels in the overlapping regions of the adjacent MR volume comprises:

maximizing a normalized cross-correlation between the overlapping regions of the adjacent MR volumes.

32. The non-transitory computer readable medium of claim 27, wherein adjusting voxel intensities in each of the plurality of slices of the composite MR volume comprises:

adjusting voxel intensities of voxels in each of the plurality of slices of the composite MR volume such that an intensity histogram of each of the plurality of slices of the composite MR volume matches an intensity histogram of the corresponding slice of the template MR volume.

33. A non-transitory computer readable medium storing computer program instructions, which, when executed on a processor, cause the processor to perform operations comprising:

receiving a plurality of magnetic resonance (MR) volumes;

generating a composite MR volume from the plurality of MR volumes; and performing volume normalization of the composite MR volume to correct intensity inhomogeneity in the composite MR volume, wherein performing volume normalization of the composite MR volume comprises:

normalizing slices of the composite MR volume along a first axis based on approximated muscle intensity in each of the slices along the first axis; and normalizing slices of the composite MR volume along a second axis based on approximated muscle intensity in each of the slices along the second axis.

34. The non-transitory computer readable medium of claim 33, wherein normalizing slices of the composite MR volume along the first axis comprises:

approximating the muscle intensity in each slice of the composite MR volume along the first axis as the median intensity of voxels in that slice; and adjusting voxel intensities in each slice of the composite MR volume along the first axis so that the approximated muscle intensity is constant along the first axis.

35. The non-transitory computer readable medium of claim 34, wherein adjusting voxel intensities in each slice of the composite MR volume along the first axis comprises:

linearly scaling a voxel intensity histogram of each slice of the composite MR volume along the first axis.

36. The non-transitory computer readable medium of claim 34, wherein normalizing slices of the composite MR volume along the second axis comprises:

approximating the muscle intensity in each slice of the composite MR volume along the second axis as the median intensity of voxels in that slice; and adjusting voxel intensities in each slice of the composite MR volume along the second axis so that the approximated muscle intensity is constant along the second axis.

37. The non-transitory computer readable medium of claim 36, wherein adjusting voxel intensities in each slice of the composite MR volume along the second axis comprises:

linearly scaling a voxel intensity histogram of each slice of the composite MR volume along the second axis.

38. The non-transitory computer readable medium of claim 36, wherein the slices of the composite MR volume along the first axis are coronal slices and the slices of the composite MR volume along the second axis are transverse slices.

39. The non-transitory computer readable medium of claim 33, wherein the first axis is an anterior-posterior axis and the second axis is a vertical axis.

* * * * *